United States Patent
Zhong et al.

(10) Patent No.: US 11,358,944 B2
(45) Date of Patent: Jun. 14, 2022

(54) ANXIOLYTIC DEUTERATED COMPOUND AND MEDICAL USE THEREOF

(71) Applicant: BEIJING JUNKE HUAYUAN MED TECH CO., LTD., Beijing (CN)

(72) Inventors: Bohua Zhong, Jiangsu (CN); Jiajun Yang, Jiangsu (CN)

(73) Assignee: BEIJING JUNKE HUAYUAN MED TECH CO., LTD., Beijing (CN)

( * ) Notice: Subject to any disclaimer, the term of this patent is extended or adjusted under 35 U.S.C. 154(b) by 128 days.

(21) Appl. No.: 16/687,538

(22) Filed: Nov. 18, 2019

(65) Prior Publication Data

US 2020/0095219 A1 Mar. 26, 2020

Related U.S. Application Data

(63) Continuation-in-part of application No. PCT/CN2018/000167, filed on May 9, 2018.

(30) Foreign Application Priority Data

May 19, 2017 (CN) .......................... 201710355025.7

(51) Int. Cl.
 C07D 307/77 (2006.01)
 A61P 25/22 (2006.01)
 A61K 9/00 (2006.01)

(52) U.S. Cl.
 CPC ............ C07D 307/77 (2013.01); A61P 25/22 (2018.01); *A61K 9/0019* (2013.01); *A61K 9/0053* (2013.01)

(58) Field of Classification Search
 CPC ...... C07D 307/77; A61P 25/22; A61K 9/0019
 USPC ......................................................... 549/458
 See application file for complete search history.

(56) References Cited

FOREIGN PATENT DOCUMENTS

| CN | 1254713 A | 5/2000 |
| CN | 1322525 A | 11/2001 |

OTHER PUBLICATIONS

Kristen C. Buteau. Deuterated Drugs (Year: 2009).*
Liu, Qian et al. Synthesis and CNS activities of alpha-agarofuran derivatives; Chinese Journal of Medicinal Chemistry; vol. 13, No. 3; Jun., 2003, Sum. 53, p. 125-130 (English Abstract on the last page).
Li, Chun et al. Synthesis of deuterium-labelled 4-butyl-alpha-agarofuran for use as an internal standard in the GC-MS method; Chinese Journal of Medicinal Chemistry; vol. 13, No. 3; Jun. 2003, Sum. 53; P148-152.

* cited by examiner

*Primary Examiner* — Taofiq A Solola
(74) *Attorney, Agent, or Firm* — Novick, Kim & Lee, PLLC; Allen Xue

(57) ABSTRACT

The present invention provides compounds as represented by structural formula (I). In formula (I), R1, R2, R3, R4, R5, R6, R7, R8, R9, R10, R11, R12, R13, and R14 are separately H or deuterium (D) independently. Moreover, at least one of R1, R2, R3, R4, R5, R6, R7, R8, R9, R10, R11, R12, R13, and R14 must be D. Also provided is use of any of the compounds or its pharmaceutical composition in the preparation of a drug for treating an anxiety.

3 Claims, No Drawings

ANXIOLYTIC DEUTERATED COMPOUND AND MEDICAL USE THEREOF

TECHNICAL FIELD

The present invention relates to a deuterated derivative of 4-butyl-α-agarofuran with an anxiolytic effect, a pharmaceutical composition containing the compound as an active ingredient, and the use of the derivative and the pharmaceutical composition thereof in the preparation of an anxiolytic agent.

BACKGROUND

Anxiety disorder is a mental disorder with persistent anxiety, fear, nervousness and autonomic dysfunction. At present, the clinical treatment drugs are mainly benzodiazepines and buspirone. The existing drugs have slow effect and large side effects, which limits their clinical application. Therefore, it is necessary to develop novel anxiolytic drugs with better efficacy and low toxicity and side effects.

4-butyl-α-agarofuran (BAF) was found through structural modification of the active constituents of agarwood and has significant anxiolytic activity. However, it has low oral bioavailability and a significant induction effect on the liver cytochrome P450 metabolic enzymes CYP1A2 and CYP2E1, which brings the risk of drug interaction (En Li, et al. Effect of buagafuran on liver microsomal cytochrome P450 in rats. J Asian Natural Products Research. 2010; 12: 371-381).

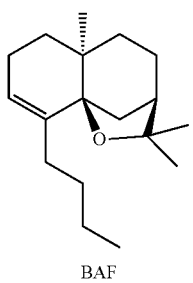 [SMILES: CCCCC1=CCC[C@@]2(C)CC[C@@H]3C[C@]12OC3(C)C]

BAF

SUMMARY

The present invention provides a compound represented by formula I:

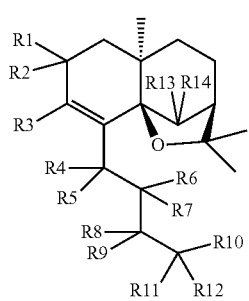

I wherein, R1, R2, R3, R4, R5, R6, R7, R8, R9, R10, R11, R12, R13 and R14 are each independently H or deuterium (D); and at least one of R1, R2, R3, R4, R5, R6, R7, R8, R9, R10, R11, R12, R13 and R14 must be D.

The present invention provides a compound represented by formula I, which is selected from the following structures:

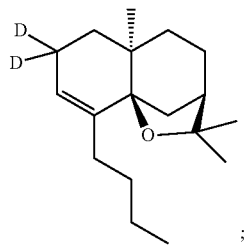

I-1

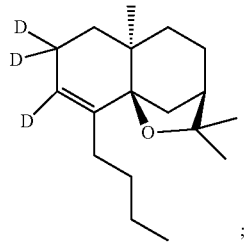

I-2

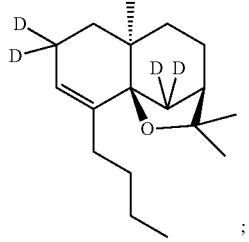

I-3

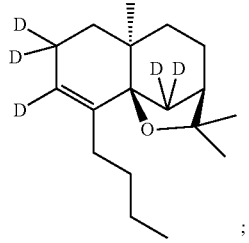

I-4

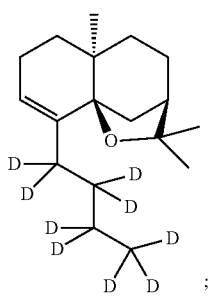

I-5

-continued

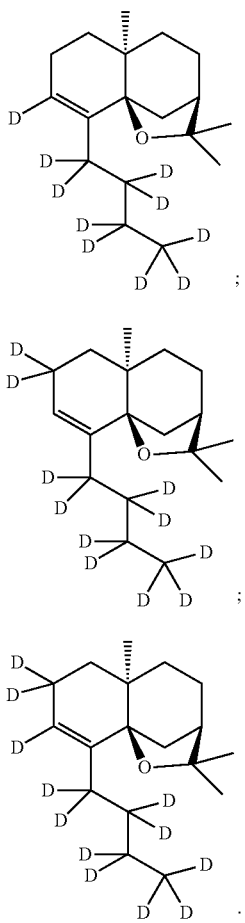

The present invention also provides a pharmaceutical composition comprising the compound represented by formula I as an active ingredient, and a suitable excipient. The pharmaceutical compositions may be solutions, tablets, capsules or injections; and the pharmaceutical compositions may be administered by injection or orally.

The present invention also provides the use of the compound represented by formula I or the pharmaceutical composition thereof for the preparation of a medicament for treating anxiety.

The present invention also provides a method for treating anxiety wherein the method comprises using the compound represented by formula I or the pharmaceutical composition thereof. The pharmaceutical compositions may be solutions, tablets, capsules or injections; and the pharmaceutical compositions may be administered by injection or orally.

DETAILED DESCRIPTION

The present invention is further described by the following examples, however, the scope of the invention is not limited to the examples described below. A person skilled in the art will appreciate that various changes and modifications can be made to the present invention without departing from the spirit and scope of the present invention.

Reference Example 1: Preparation of 4-butyl-α-agarofuran (BAF)

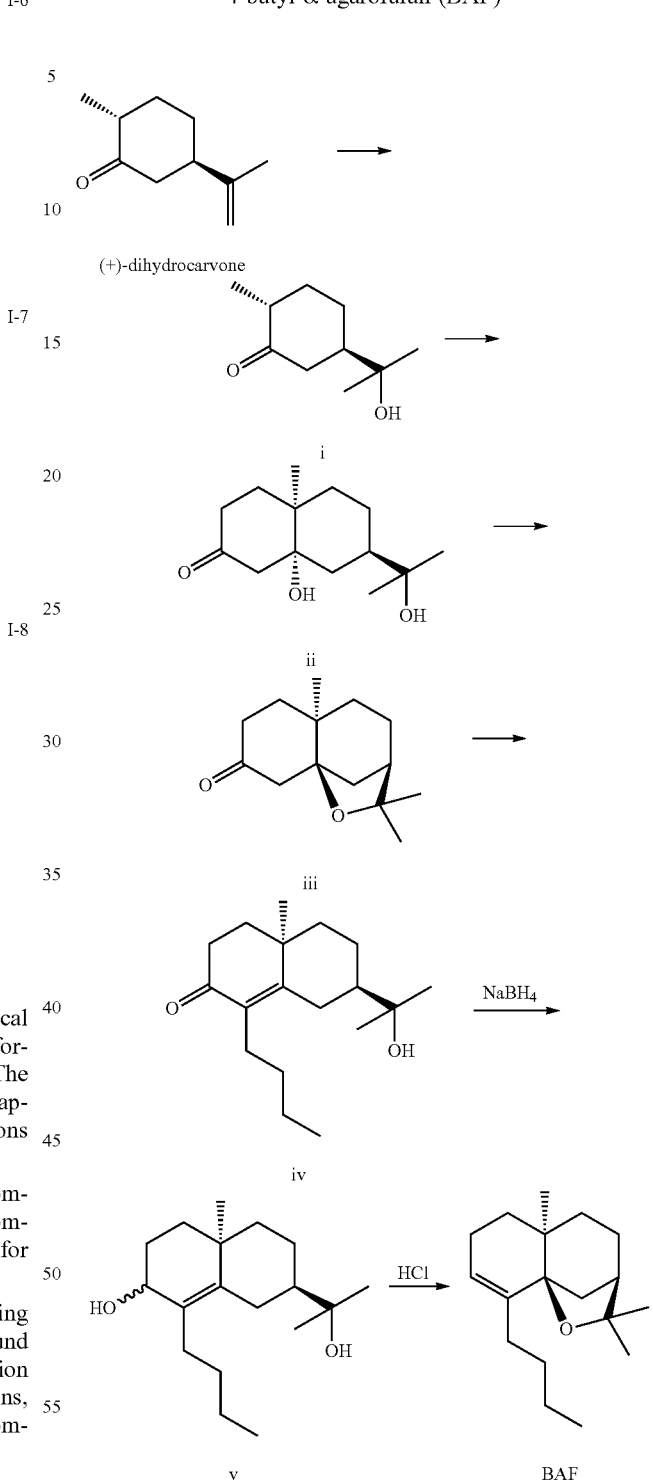

Reference Example 1.1: Preparation of Intermediate i 20 g (+)-dihydrocarvone was added to 100 ml 4.6 M sulfuric acid, stirred at room temperature for 12 h, then extracted with 20 ml of n-hexane, and then the aqueous layer was extracted with dichloromethane (50 ml×2). The dichloromethane extract was combined, washed with water until neutral, dried over anhydrous sodium sulfate and filtered out solid. The filtrate was evaporated under reduced pressure with the removal of solvent, and separated by silica gel column chromatography using a mixture of petroleum ether: ethyl acetate (8:2) as an eluent. The desired fractions were collected, and evaporated under reduced pressure to dryness to give 18 g i.

Reference Example 1.2: Preparation of Intermediate ii 2.3 g potassium hydroxide was added to 50 ml 95% ethanol, added with a solution of 17 g i in 50 ml isopropyl ether while stirring, then stirred, cooled to −10° C., and added dropwise with 8.4 g methyl vinyl ketone within 1.5 hours. After the addition was completed, stirring was continued for 30 minutes. 6 M hydrochloric acid was added dropwise to the reaction mixture to make pH neutral under the ice bath. The precipitate was collected by filtration, washed with isopropyl ether and evaporated under reduced pressure to dryness to give 8.2 g ii.

Reference Example 1.3: Preparation of Intermediate iii 300 ml water and 250 ml petroleum ether were added to a 1000 ml flask, and added with 8 g ii and 22.4 g KOH successively while stirring, heated and stirred for 5 hours in an oil bath of 70-80° C. The reaction mixture was cooled to room temperature. The petroleum ether layer was separated, neutralized with 1M hydrochloric acid, washed with brine, and evaporated with the removal of solvent, and separated by silica gel column chromatography using a mixture of petroleum ether:ethyl acetate (10:1 to 3:1) for gradient elution. The desired fractions were collected, and evaporated under reduced pressure to dryness to give 4.5 g iii.

Reference Example 1.4: Preparation of Intermediate iv 0.84 g potassium was added to 30 ml tert-butanol, after dissolving, added with 4 g iii and heated to reflux. 2.5 g n-butyl bromide was added dropwise to 10 ml n-butanol, and the addition was completed in 20 minutes. Stirring was continued for 15 minutes. The reaction mixture was cooled to 0° C., diluted with 20 ml water, neutralized with 1 M hydrochloric acid. The organic layer was removed by evaporating under reduced pressure, and the residual was extracted with 50 ml ethyl acetate, dried over anhydrous sodium sulfate, and filtered out solid. The filtrate was evaporated under reduced pressure with the removal of solvent, and separated by silica gel column chromatography using a mixture of petroleum ether:ethyl acetate (10:1) as an eluent, to give 3.1 g iv.

Reference Example 1.5 Preparation of Intermediate v 0.56 g iv was added to 10 ml methanol, dissolved by stirring, then added with 0.16 g NaBH$_4$. The reaction mixture was stirred and reacted for 3 hours. The reaction mixture was under the ice bath and neutralized with 1M hydrochloric acid. The organic layer was evaporated under reduced pressure and the residue was extracted with 20 ml ethyl acetate, and the extract was washed with brine, dried over anhydrous sodium sulfate, and filtered out solid. The filtrate was evaporated under reduced pressure with the removal of solvent and the obtained crude of v was used directly in the next step.

Reference Example 1.6 Preparation of BAF 0.56 g crude product of v was added to 10 ml methanol, stirred to dissolve, added with 10 ml 1 M hydrochloric acid and 20 ml petroleum ether successively, and stirred for 3 hours. The organic layer was separated and washed successively with 1M NaOH and brine, then dried over anhydrous sodium sulfate and filtered out solid. The filtrate was evaporated under reduced pressure with the removal of solvent, and separated by silica gel column chromatography using a mixture of petroleum ether:ethyl acetate (40:1) as an eluent. The desired fractions were collected, and evaporated under reduced pressure to dryness to give 0.3 g BAF. $[\alpha]^{20}_D$=+16.9 (c:1.3, acetone). Nuclear magnetic resonance hydrogen spectrum: $^1$H-NMR (400 MHz, CDCl$_3$): 0.89 (s, 3H); 0.90 (s, 3H); 1.04 (m, 1H); 1.18 (m, 1H); 1.25-1.29 (m, 4H); 1.36 (s, 3H); 1.41-1.75 (m, 8H); 1.92-2.00 (m, 5H); 2.21 (dd, 1H); 5.58 (br, 1H).

Example 1 Preparation of d$_2$-BAF (I-1)

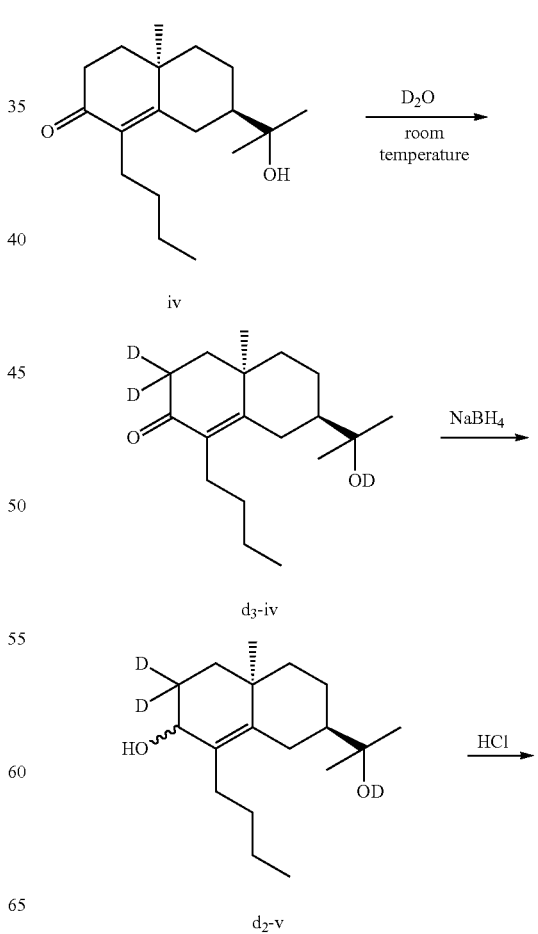

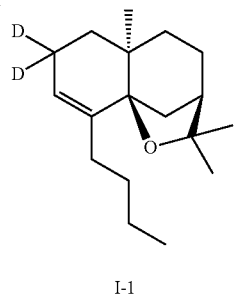

I-1

Example 1.1 Preparation of Intermediate d₃-iv 5 ml D₂O (abundance: 99.5%) was taken, added with anhydrous potassium carbonate to pH 10, then added with 5 ml CH₃OD (abundance: 99.5%); added with a solution of 0.8 g iv dissolved in 5 ml CH₃OD (abundance: 99.5%), stirred at 25° C. for 3 hours, evaporated to dryness under reduced pressure, added with 5 ml D₂O (abundance: 99.5%), adjusted to pH=10 with anhydrous potassium carbonate, then added with 5 ml CH₃OD (abundance: 99.5%), stirred at 25° C. for 3 hours and evaporated to dryness under reduced pressure to give the crude product of d₃-iv.

Example 1.2 Preparation of Intermediate d₂-v 10 ml CH₃OD (abundance: 99.5%) was added to the crude product of d₃-iv, stirred, and filtered; 0.15 g NaBH₄ was added to the filtrate, stirred and reacted for 3 hours; The reaction solution was under the ice bath and neutralized with 1 M hydrochloric acid. The organic layer was removed by evaporating under reduced pressure. The residual was extracted by 20 ml ethyl acetate, washed with brine, then dried over anhydrous sodium sulfate, filtered out solid, evaporated under reduced pressure with the removal of solvent, and separated by silica gel column chromatography using a mixture of petroleum ether:ethyl acetate (10:1) as an eluent. The desired fractions were collected, and evaporated under reduced pressure to dryness to give 0.32 g d₂-v.

Example 1.3 Preparation of Target Compound I-1

0.32 g d₂-v was dissolved in 5 ml methanol, added with 5 ml 1 M hydrochloric acid and 10 ml petroleum ether successively under stirring, and stirred for 3 hours. The organic layer was separated and washed with 1M NaOH and brine successively. The organic layer was dried over anhydrous sodium sulfate, filtered out solid, evaporated under reduced pressure with the removal of solvent, and separated by silica gel column chromatography using a mixture of petroleum ether:ethyl acetate (40:1) as an eluent. The desired fractions were collected, and evaporated under reduced pressure to dryness to give 0.25 g I-1. $[\alpha]^{20}_D$=+16.7 (c: 1.3, acetone). Nuclear magnetic resonance hydrogen spectrum: ¹H-NMR (400 MHz, CDCl₃): 0.89 (s, 3H); 0.90 (s, 3H); 1.04 (m, 1H); 1.18 (m, 1H); 1.24-1.28 (m, 4H); 1.36 (s, 3H); 1.41-1.75 (m, 8H); 1.95-2.01 (m, 3H); 2.21 (dd, 1H); 5.57 (s, 1H). The abundance of deuterium was 98.6%, determined by mass spectrometry.

Example 2 Preparation of d₃-BAF (I-2)

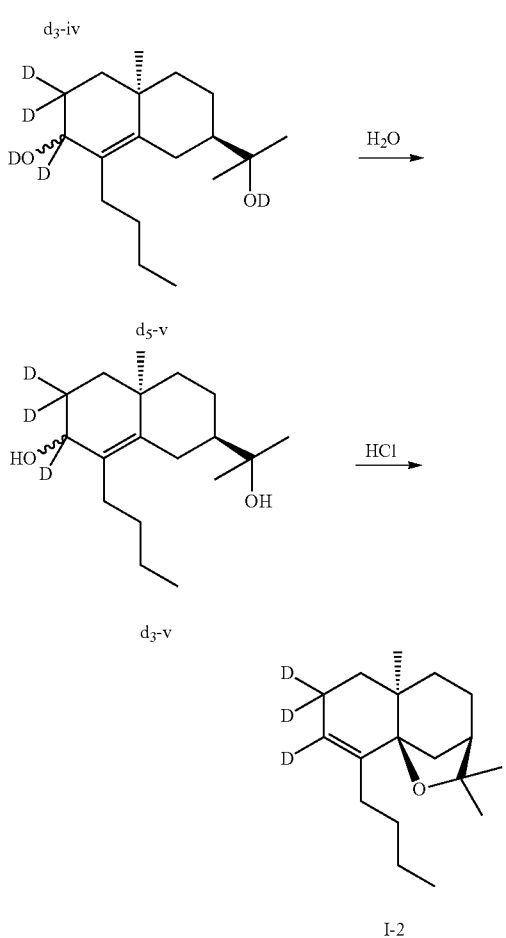

D₃-iv was reduced with NaBD₄ (abundance of deuterium: 98%) according to the method of Example 1.2 to obtain d₃-v.

Referring to the method of Example 1.3, d₃-v was reacted with 1 M hydrochloric acid to obtain I-2. $[\alpha]^{20}_D$=+16.7 (c: 1.3, acetone). ¹H-NMR (400 MHz, CDCl₃): 0.89 (s, 3H); 0.90 (s, 3H); 1.04 (m, 1H); 1.18 (m, 1H); 1.24-1.28 (m, 4H);

1.36 (s, 3H); 1.41-1.75 (m, 8H); 1.95-2.01 (m, 3H); 2.22 (dd, 1H). The abundance of deuterium was 98.2%, determined by mass spectrometry.

Example 3 Preparation of $d_4$-BAF (I-3)

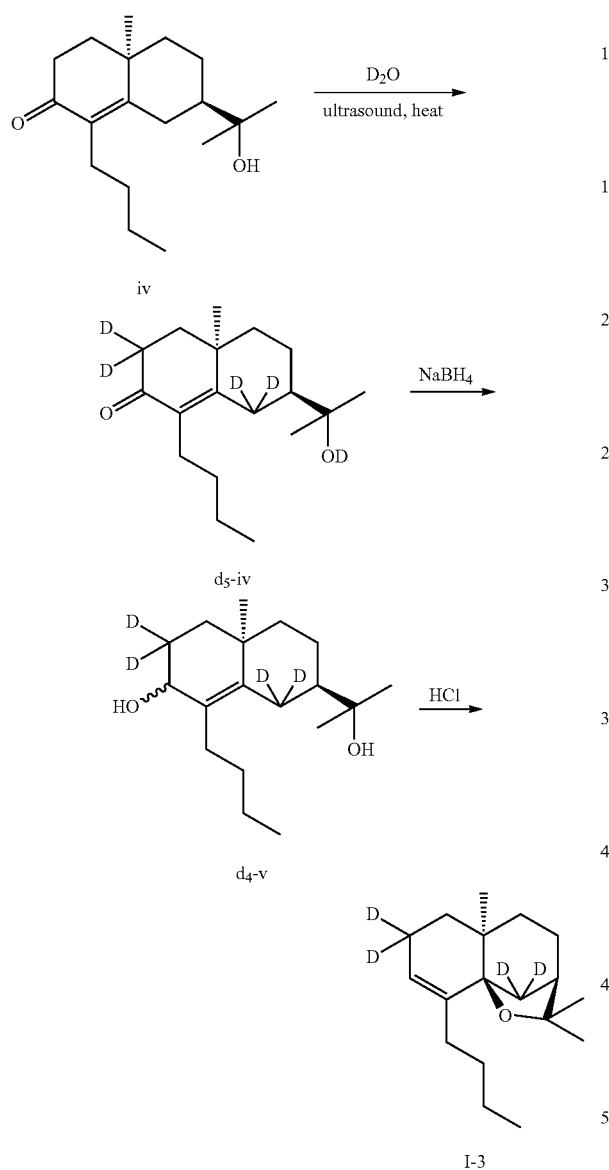

Example 3.1 Preparation of Intermediate $d_5$-iv 5 ml $D_2O$ (abundance: 99.5%) was taken, added with anhydrous potassium carbonate to pH 10, then added with 5 ml $CH_3OD$ (abundance: 99.5%); added with a solution of 0.8 g iv dissolved in 5 ml $CH_3OD$ (abundance: 99.5%), stirred under ultrasound at 35° C. for 3 hours; evaporated under reduced pressure to dryness, added with 5 ml $D_2O$ (abundance: 99.5%), adjusted to pH=10 with anhydrous potassium carbonate, then added with 5 ml $CH_3OD$ (abundance: 99.5%), stirred under ultrasound at 35° C. for 3 hours; evaporated under reduced pressure to dryness to give the crude product of $d_5$-iv.

Example 3.2 Preparation of Intermediate $d_4$-v $d_{5\text{-}iv}$ was reduced with $NaBH_4$ to obtain $d_4$-v, referring to the method of Example 1.2.

Example 3.3 Preparation of Target Compound I-3

Referring to the method of Example 1.3, $d_4$-v was reacted with hydrochloric acid to obtain I-3. $[\alpha]^{20}_D$=+16.7 (c: 1.3, acetone). Nuclear magnetic hydrogen resonance spectroscopy: $^1$H-NMR (400 MHz, CDCl$_3$): 0.89 (s, 3H); 0.90 (s, 3H); 1.18 (m, 1H); 1.24-1.28 (m, 4H); 1.36 (s, 3H) 1.41-1.75 (m, 8H); 1.95-2.01 (m, 3H); 5.59 (s, 1H). The abundance of deuterium was 98.4%, determined by mass spectrometry.

Example 4 Preparation of $d_5$-BAF (I-4)

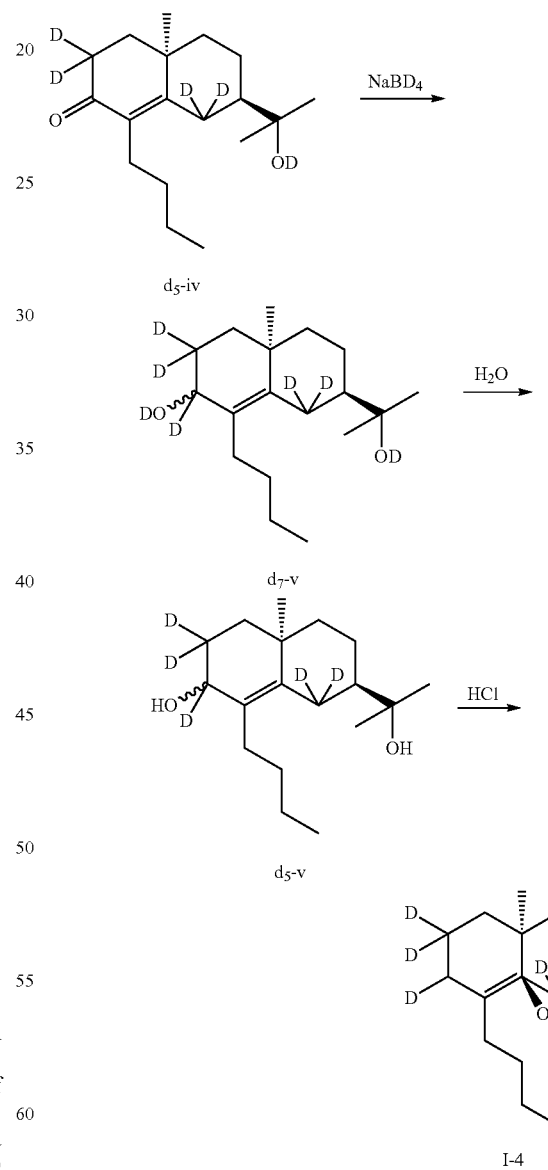

Referring to the method of Example 1.2, $d_5$-iv was reduced with $NaBD_4$ to obtain $d_5$-v.

Referring to the method of Example 1.3, $d_5$-v was reacted with hydrochloric acid to obtain I-4. $[\alpha]^{20}$D=+16.7 (c: 1.3, acetone). Nuclear magnetic hydrogen resonance spectroscopy: $^1$H-NMR (400 MHz, CDCl$_3$): 0.89 (s, 3H); 0.90 (s, 3H); 1.19 (m, 1H); 1.24-1.28 (m, 4H); 1.36 (s, 3H) 1.41-1.75 (m, 8H); 1.95-2.01 (m, 3H). The abundance of deuterium was 98.1%, determined by mass spectrometry.

Example 5 Preparation of d$_9$-BAF (I-5)

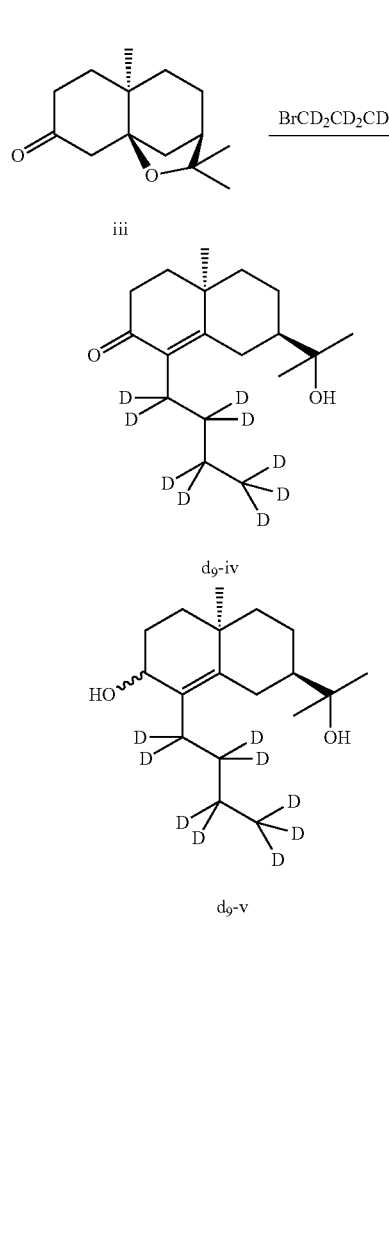

Example 6 Preparation of d$_{10}$-BAF (I-6)

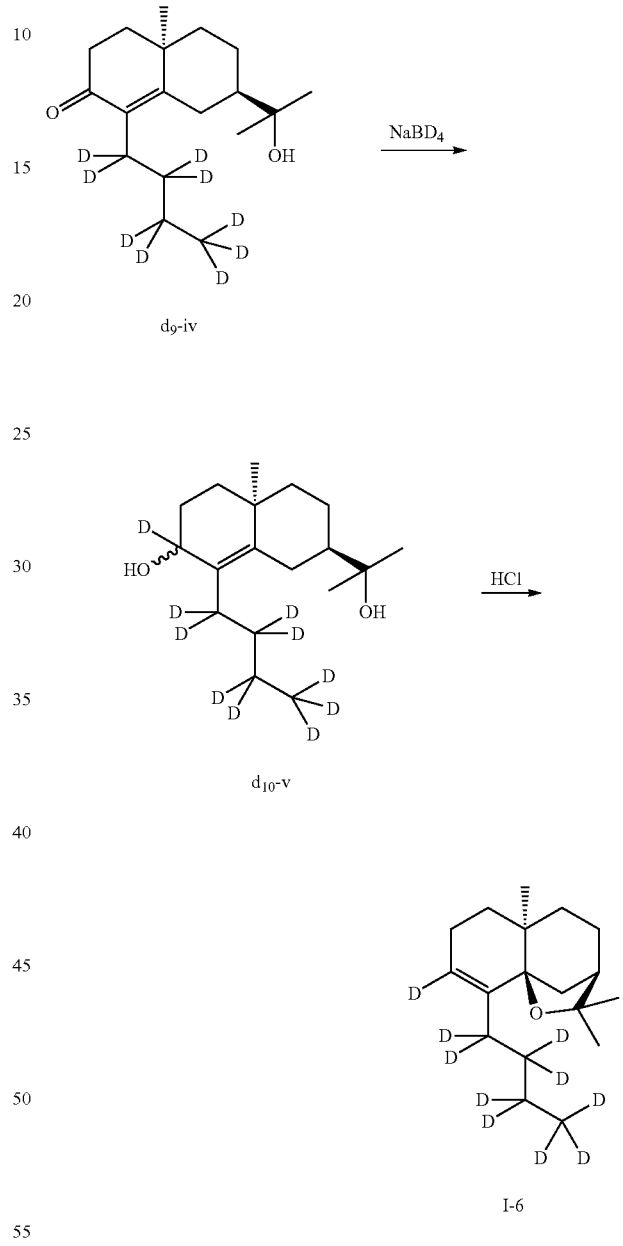

d$_9$-iv was prepared by reacting iii with BrCD$_2$CD$_2$CD$_2$CD$_3$ (abundance of deuterium: >98%), referring to the method of Reference Example 1.4.

Referring to the method of Reference Example 1.5, d$_9$-iv was reduced with NaBH$_4$ to obtain d$_9$-v.

Referring to the method of Reference Example 1.6, d$_9$-v was reacted with 1 M hydrochloric acid to obtain I-5. $[\alpha]^{20}_D$=+16.8 (c:1.3, acetone). Nuclear magnetic hydrogen resonance spectroscopy: $^1$H-NMR (400 MHz, CDCl$_3$): 0.89 (s, 3H); 1.03 (m, 1H); 1.18 (m, 1H); 1.24-1.28 (m, 4H); 1.36 (s, 3H); 1.41-1.75 (m, 4H); 1.92-2.01 (m, 3H); 2.21 (dd, 1H); 5.59 (br, 1H). The abundance of deuterium was 98.1%, determined by mass spectrometry.

Referring to the method of Example 1.2, d$_9$-iv was reduced with NaBD$_4$ (abundance of deuterium: 98%) to prepare d$_{10}$-v.

Referring to the method of Example 1.3, d$_{10}$-v was reacted with 1 M hydrochloric acid to obtain I-6. $[\alpha]^{20}_D$=+16.9 (c: 1.3, acetone). Nuclear magnetic hydrogen resonance spectroscopy: $^1$H-NMR (400 MHz, CDCl$_3$): 0.89 (s, 3H); 1.04 (m, 1H); 1.17 (m, 1H); 1.24-1.28 (m, 4H); 1.36 (s, 3H); 1.42-1.75 (m, 4H); 1.92-2.00 (m, 3H); 2.22 (dd, 1H). The abundance of deuterium was 98.1%, determined by mass spectrometry.

Example 7 Preparation of $d_{11}$-BAF (I-7)

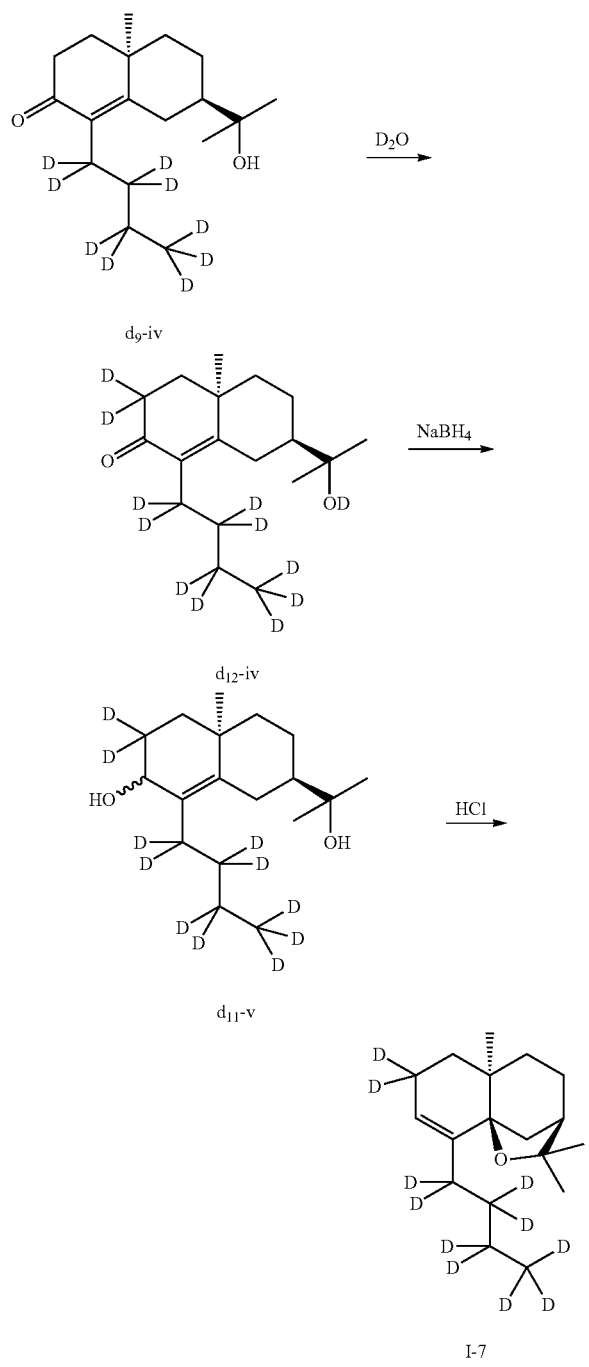

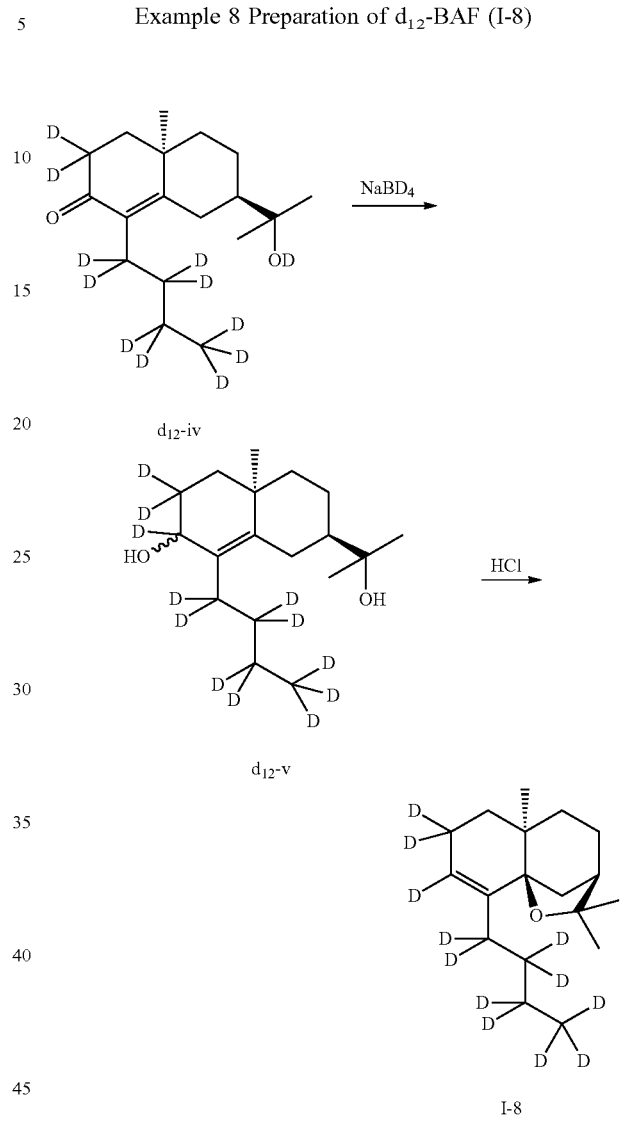

1.41-1.75 (m, 4H); 1.92-2.02 (m, 1H); 2.20 (dd, 1H); 5.59 (s, 1H). The abundance of deuterium was 98.2%, determined by mass spectrometry.

Example 8 Preparation of $d_{12}$-BAF (I-8)

$d_{12}$-iv was reduced with $NaBD_4$, referring to the method of Example 1.2 to obtain $d_{12}$-v.

Referring to the method of Example 1.3, $d_{12}$-v was reacted with 1 M hydrochloric acid to obtain I-8. $[\alpha]^{20}_D=+16.7$ (c: 1.3, acetone). Nuclear magnetic hydrogen resonance spectroscopy: $^1$H-NMR (400 MHz, $CDCl_3$): 0.89 (s, 3H); 1.03 (m, 1H); 1.18 (m, 1H); 1.23-1.28 (m, 4H); 1.36 (s, 3H) 1.42-1.77 (m, 4H); 1.92-2.01 (m, 1H); 2.21 (dd, 1H). The abundance of deuterium was 98.1%, determined by mass spectrometry.

Example 9 Evaluation of Anxiolytic Effect

The anxiolytic effect of the compounds was evaluated using an elevated plus-maze test on rats.

The elevated plus-maze consists of two closed arms and two open arms cross each other with length, width and height respectively of 50 cm, 10 cm and 40 cm.

The central connecting area is 10 cm (length)×10 cm (width), and the maze is 50 cm above the ground, placed in Referring to the method of Example 1.1, $d_9$-iv was subjected to a reaction of heavy water exchange with $D_2O$ to obtain $d_{12}$-iv.

Referring to the method of Example 1.2, $d_{12}$-iv was reduced with $NaBH_4$ to give $d_{11}$-v.

Referring to the method of Example 1.3, $d_{11}$-v was reacted with 1 M hydrochloric acid to obtain I-7. $[\alpha]^{20}D=+16.8$ (c: 1.3, acetone). Nuclear magnetic hydrogen resonance spectroscopy: $^1$H-NMR (400 MHz, $CDCl_3$): 0.89 (s, 3H); 1.04 (m, 1H); 1.19 (m, 1H); 1.25-1.27 (m, 4H); 1.36 (s, 3H);

the darker side of the fluorescent lamp and 1 meter away from the lamp. Wistar rats were randomly divided into groups with 5 per group, and the rats were fasted but not deprived of water for 12 hours; The test compound was formulated with 0.5% sodium carboxymethylcellulose into a suspension of certain concentration for intragastric administration. Thirty minutes after administration, the rats were placed in the central connecting area of the maze with the heads facing the direction of the open arms. Then the dwell time of the animals in the open arms within 5 minutes was recorded. The results are shown in Table 1:

TABLE 1

Anxiolytic effect of the target compound for intragastric administration

| Drug | dwell time in the open arms (seconds) | | |
|---|---|---|---|
| | 1 mg/kg | 2 mg/kg | 4 mg/kg |
| BAF | 26.7 ± 27.0 | 45.2 ± 39.7 | 69.0 ± 49.0 |
| I-1 | 48.6 ± 21.7 | 68.4 ± 30.8 | 47.5 ± 23.6 |
| I-2 | 45.6 ± 19.1 | 69.7 ± 29.8 | 39.0 ± 25.7 |
| I-3 | 52.5 ± 26.0 | 67.2 ± 22.0 | 42.7 ± 25.1 |
| I-4 | 62.3 ± 32.4 | 66.8 ± 30.8 | 44.5 ± 29.5 |
| I-5 | 72.0 ± 15.8 | 71.2 ± 15.3 | 76.5 ± 16.0 |
| I-6 | 73.3 ± 17.6 | 71.4 ± 19.1 | 66.3 ± 19.6 |
| I-7 | 77.5 ± 23.3 | 72.6 ± 18.6 | 73.8 ± 11.0 |
| I-8 | 70.7 ± 23.2 | 76.9 ± 14.4 | 72.3 ± 17.8 |

Example 10 Evaluation of Subacute Toxicity and Induction Effect of Metabolic Enzyme Male Sprague-Dawley rats (220-240 g), were randomly divided into groups with 5 per group; The test compound was formulated with 0.5% sodium carboxymethylcellulose into a preparation of a concentration of 60 mg/kg for intragastric administration once a day and continuously for 7 days. After the last administration, the SD rats were fasted but not deprived of water for 12 hours, and anesthetized. Their blood samples were obtained from the abdominal aortas and made to serum samples for determination of blood biochemical indicators and immunological indicators; EDTA Anticoagulated blood was prepared for general blood routine determination. Referring to the method of the literature (En Li, et al. Effect of buagafuran on liver microsomal cytochrome P450 in rats. J Asian Natural Products Research. 2010; 12: 371-381.), liver microsome was prepared from the liver taken, and the activity of CYP isoenzyme was determined using a probe substrate. The relative enzymatic activity of the test compound was calculated by taking the activity of the solvent group as 1.

Example 10.1 Evaluation Results of Subacute Toxicity

The results of 14 hematological indexes and 15 plasma biochemical indicators show that plasma ALT and AST were significantly increased in BAF group while there were no significant differences between plasma ALT, AST of groups I-1, I-2, I-5, I-7 and that of control group (Solvent group). The results are shown in Table 2. The other indicators of each group of the animals are in the normal range.

TABLE 2

Effect of continuous administration of the target compound on transaminase

| Drug | ALT (U/L) | AST (U/L) |
|---|---|---|
| Solvent group | 74.5 | 124.1 |
| BAF | 189.0 | 258.7 |
| I-1 | 116.1 | 163.9 |
| I-2 | 74.0 | 115.4 |
| I-5 | 56.6 | 137.2 |
| I-7 | 48.7 | 107.7 |

Example 10.2 Evaluation Results of Induction Effect of Metabolic Enzymes

Compared with the solvent group, the activity of the metabolic enzymes CYP1A1 and CYP2E1 in the livers of the animals of BAF group was significantly increased. The activity of the metabolic enzymes CYP1A1 and CYP2E1 in the livers of the animals of the I-1, I-2, I-5 and I-7 groups was not significantly different from that of the solvent group. The activity of the metabolic enzymes CYP2C11, CYP2C6, CYP2D2, and CYP3A2 of each group were not significantly different from that of the solvent group. The results are shown in Table 3:

TABLE 3

Relative enzyme activity of continuous administration of the target compound

| Drug | CYP1A1 | CYP2E1 |
|---|---|---|
| Solvent group | 1 | 1 |
| BAF | 3.8 | 1.7 |
| I-1 | 1.7 | 1.2 |
| I-2 | 1.4 | 1.0 |
| I-5 | 1.3 | 1.2 |
| I-7 | 1.1 | 0.9 |

The invention claimed is:

1. A compound, which is selected from compounds of formula (I-5) and formula (I-7):

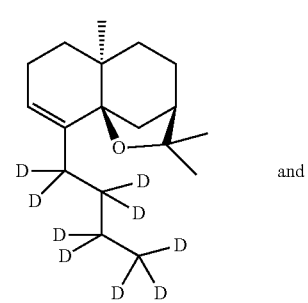

and

-continued
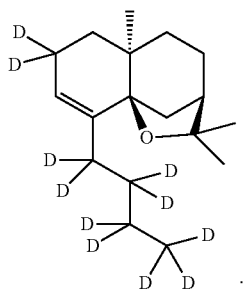
I-7
2. A pharmaceutical composition, comprising a compound of claim 1 as an active ingredient, and one or more pharmaceutically acceptable carriers or excipients.
3. A method for treating anxiety, comprising administering a pharmaceutical composition comprising a compound of claim 1 to a subject in need thereof.
* * * * *